United States Patent [19]
Steffen et al.

[11] 4,216,153
[45] Aug. 5, 1980

[54] METHOD OF PREPARING PHTHALIDE

[75] Inventors: Klaus D. Steffen, Hennef; Fritz Englaender, Bonn-Bad Godesberg, both of Fed. Rep. of Germany

[73] Assignee: Dynamit Nobel Aktiengesellschaft, Troisdorf, Fed. Rep. of Germany

[21] Appl. No.: 931,075

[22] Filed: Aug. 4, 1978

[30] Foreign Application Priority Data

Aug. 6, 1977 [DE] Fed. Rep. of Germany ....... 2735503

[51] Int. Cl.² ............................................. C07D 307/88
[52] U.S. Cl. ...................... 260/343.3 R; 204/158 HA
[58] Field of Search .................... 260/343.3 R, 651 R; 204/158 HA

[56] References Cited

U.S. PATENT DOCUMENTS

| 3,223,728 | 12/1965 | Di Bella | 260/651 R |
|---|---|---|---|
| 3,350,467 | 10/1967 | Lasco | 260/651 R |
| 3,663,575 | 5/1972 | Roos | 260/343.3 R |
| 4,113,741 | 9/1978 | Fünten | 260/343.3 R |
| 4,116,976 | 9/1978 | Englander et al. | 260/343.3 R |

OTHER PUBLICATIONS

Hjelt, Ber. 19 (1886) p. 412.
Wagner et al., Synthetic Organic Chem., p. 535, John Wiley & Sons Inc., New York.
Rabjohn, Jour. Amer. Chem. Soc., 76, 1954, pp. 5479-5482.

*Primary Examiner*—Natalie Trousof
*Assistant Examiner*—Jane T. Fan
*Attorney, Agent, or Firm*—Sprung, Felfe, Horn, Lynch & Kramer

[57] ABSTRACT

A method has been invented for the preparation of phthalide which comprises chlorinating o-toluic acid at 30°–260° C. and recovering the phthalide obtained.

1 Claim, 2 Drawing Figures

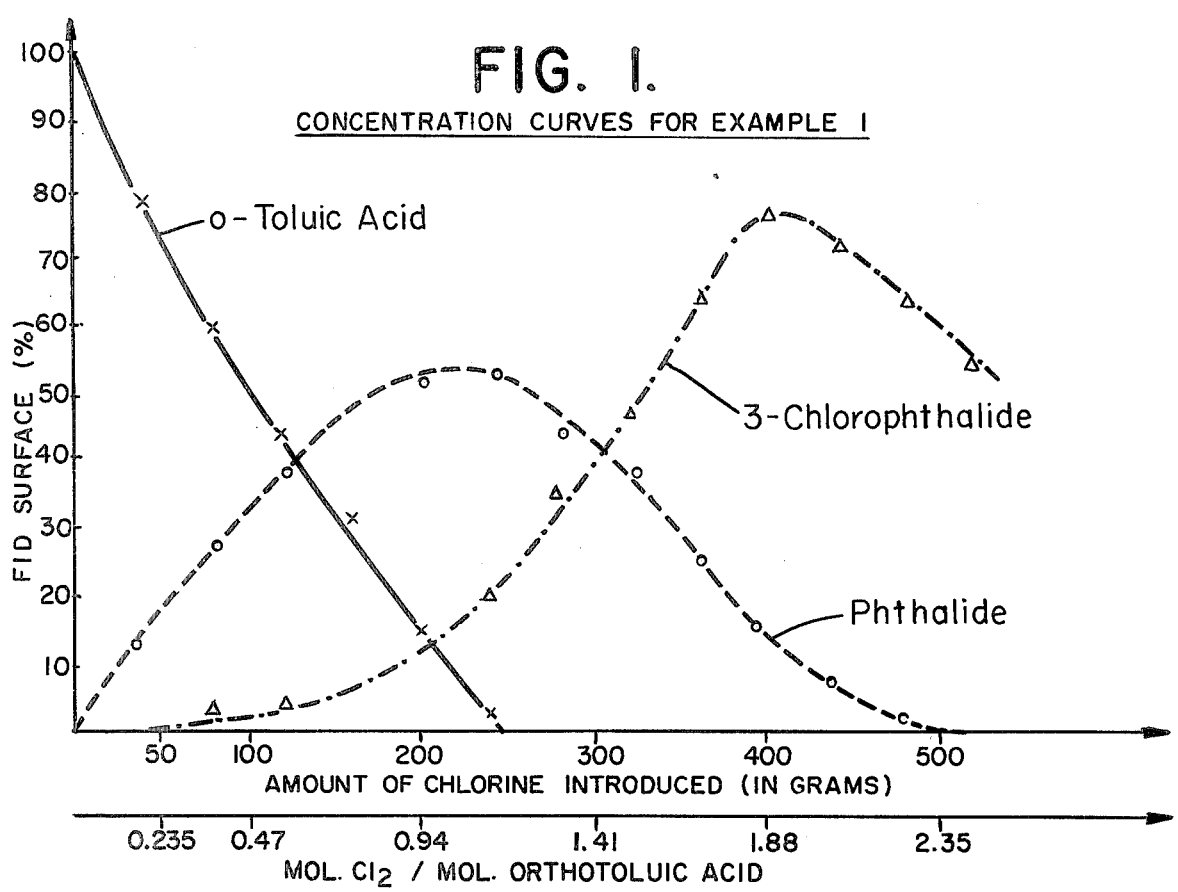
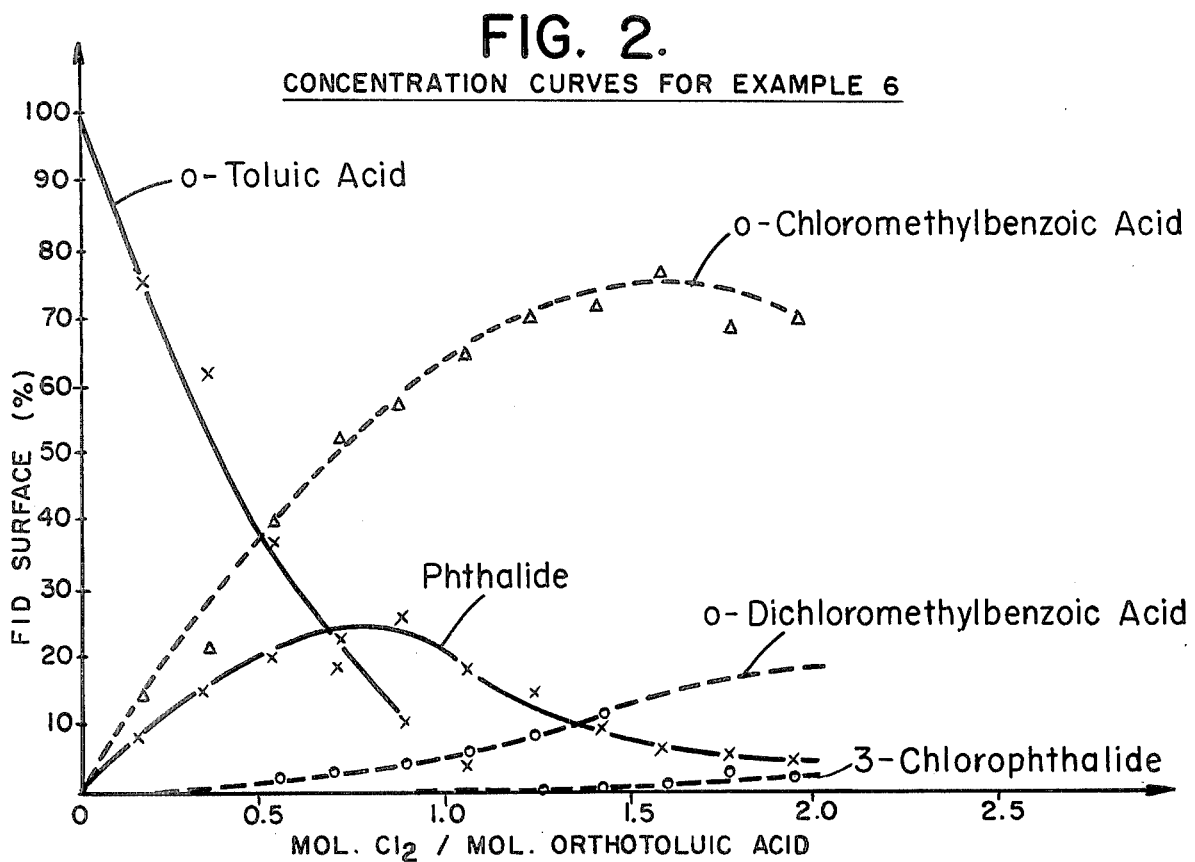

METHOD OF PREPARING PHTHALIDE

BACKGROUND

The subject matter of the invention is a method of preparing phthalide by the chlorination of o-toluic acid at elevated tempreatures and processing the chlorination mixture to phthalide, wherein, if any o-chloromethyl benzoic acid or o-dichloromethylbenzoic acid is present it is cyclized to phthalide or 3-chlorophthalide, and if there is any 3-chlorophthalide present it is hydrogenated to phthalide.

Phthalide, which is also known as 1-(3H)-isobenzofuranone, is known, and it is desired as an intermediate for pharmaceutical chemistry, for example for the synthesis of bromophthalide which is required for penicillin and cephalosporin derivatives. Phthalide is also used directly as an anthelmintic. Phthalide is also useful for the synthesis of anthraquinone dyes.

A number of methods of preparation have been described (Beilstein, System No. 2463, vol. 17, p. 310, Erg. Bd. 17 I, p. 161, II, p. 332, III & IV, p. 4948). Many authors set out from o-xylols polysubstituted with oxygen or halogen, e.g., from phthalic aldehyde, phthalyl alcohol, α-di- to tetrachlorozylenes, but also 2-cyanobenzyl halide among others. Toluic acid derivatives can be hydrolyzed oxidatively to phthalide, using lead or copper nitrate solutions, chromic acid, nitric acid, potassium persulfate, and the like as oxidants; hydrolyses often have to be performed at 200° C. under pressure.

Disadvantages of these methods are the expensive starting materials, the usually insufficient purity of the phthalide, the necessity of stoichiometric amounts of the oxidants, and the production of large amounts of solutions of the used oxidants.

Other investigators have produced phthalide from phthalic acid anhydride by reduction, for example with zinc dust in hydrochloric acid or acetic acid, and also with LiAlH$_4$, sodium boranate, sodium amalgam, or with a mixture of hydrogen iodide and yellow phosphorus. In the reduction with zinc dust in acetic acid, undesirable by-products are formed, such as diphthalyl, hydrodiphthalyl and α-(phthalidyl-3)-o-toluic acid, plus the undesirable ZnCl$_2$. The other reductants are expensive laboratory chemicals and are difficult to handle. In technical processes they would be uneconomical.

Catalytic hydrogenations of phthalic acid anhydride (PAA) are performed at high temperatures of 150° to 600° C. and high pressures of 85 to 300 atmospheres, using catalysts such as nickel, platinum, aluminum, or copper chromic oxide. These pressure hydrogenations call for complex apparatus and give unclean products in unsatisfactory yields, sometimes containing dissolved catalysts.

In the electrochemical reduction of German Auslegeschrift 21 44 419, phthalic acid anhydride is first transformed to ammonium phthalamate, a solution of which (in a mixture of water and organic solvent) is reduced on a lead cathode. This process requires a complex apparatus, special knowledge and costly electrically power.

Other methods which can be used only in the laboratory produce phthalide by reduction from phthalimide or from N-nitrosophthalimidine (Houben-Weyl O/2, pp. 735–736).

In a brief report containing no information on yeild, E. Hjelt, in Ber. 19 (1886) 412, describes the bromination of o-toluic acid to phthalide at 140° C. When its reproduction was attempted it was found that at no time is phthalide present in concentrations of more than 20%, and accordingly it is transformed preferentially, further, to bromophthalide. Due to the large amounts of the by-products, toluic acid, bromophthalide, 3-(o-carboxybenzyl)-phthalide and others, phthalide is obtained only with difficulty and in very low yields, and it is furthermore heavily contaminated, especially by hard-to-remove substances which are formed by the oxidative action of bromine.

THE INVENTION

The problem, therefore, has existed of preparing phthalide from inexpensive mass chemicals in a reasonable purity and yield by a method which can be practiced in a technically simple manner in apparatus and vessels which are commonly used in the chemical industry.

It has been found that, in the chlorination of o-toluic acid at slightly elevated temperatures, first o-chloromethyl benzoic acid is formed and, as additional chlorine is supplied, o-dichloromethylbenzoic acid is formed, from which, when the temperature is increased to above 100° C., phthalide and 3-chlorophthalide are formed. If still higher temperatures of about 120° C. and more are used, little or no chlorotoluic acids are formed. The lower the chlorination temperature is, the greater are the concentrations in which the chloromethylbenzoic acids are formed (see Examples 5, 6, 10 and 11).

According to thermogravimetric tests, the splitting off of HCl and with it cyclization to the phthalide ring begins at about 105° C. for o-chloromethylbenzoic acid, and at about 115° C. for o-dichloromethylbenzoic acid.

Formally, the reaction takes place as follows:

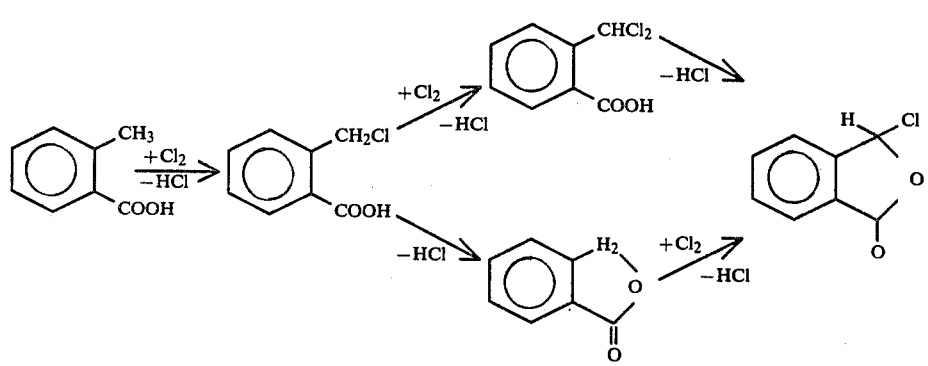

At 160° C. chlorination temperature, the sum of the concentrations of o-chloromethylbenzoic and o-dichloromethylbenzoic acid never exceeds 2.5% throughout the entire chlorination. At 180° C. it is still only about 1.5%.

Since the chlorination mixture, therefore, has different compositions depending on the conditions of its preparation, a variety of working-up processes are required which are mainly based on separating the phthalide from the o-toluic acid or 3-chlorophthalide starting products and, in the ideal case, to transform the by-products insofar as possible to phthalide—the target product—or to keep the concentrations of the by-products that cannot be converted as low as possible.

The subject matter of the invention, therefore, is a method for the preparation of phthalide which is characterized in that o-toluic acid is chlorinated under the conditions of side-chain chlorination at temperatures from 30° to 260° C., and the phthalide is isolated and recovered from the chlorination mixture, in some cases after the cyclization of o-chloro- and o-dichloromethylbenzoic acid to phthalide or 3-chlorophthalide and the transformation of 3-chlorophthalide by catalytic hydrogenation to phthalide.

The starting substances for the process are easily available, since chlorine is an inexpensive gaseous chemical which is produced in excess. o-Toluic acid is a mass chemical which can be obtained cheaply from o-xylene by partial oxidation with air.

The apparatus consists of simple stirring tanks with internal deflectors, inlets and outlets for gases, and a hydrogen chloride absorber, that is to say, conventional, easily obtainable apparatus.

For the chlorination, temperature can vary between 30° and 260° C.; there are two preferred ranges, one between 110° and 260°, especially between 150° and 240° C., and the other between 30° and 110° C., especially up to 90° C. The high temperatures are to be preferred, since at these temperatures the substance selectivity for phthalide and chlorophthalide, the distinctness of the concentration curves from one another, and the differences between the individual concentration maxima and hence the separation of the individual components is particularly advantageous (see Examples 1 to 6). This is a discovery contrary to the general conception that selectivity normally decreases as the temperature increases.

The second preferred range, therefore, is 30° to 90° C., because at these low temperatures the o-chloromethylbenzoic acid content can be increased to 70 to 80% plus about 10% phthalide, and since the o-chloromethylbenzoic acid can afterward by cyclized to the phthalide target product by increasing the temperature to about 120° to 150° C. or more in some cases, with the yielding of HCl. At these low chlorination temperatures, therefore, a chlorination mixture is obtained of which 90% already consists of phthalide in capped preliminary form.

If the chlorination is performed in the melt, a range of 107° to 250° C. is then fundamentally possible. The chlorination can also be performed in inert solvents which do not react with chlorine. For the upper, preferred temperature range, those solvents are to be preferred which have high boiling points above about 120° C., such as o-dichlorbenzene or hexachlorobutadiene, since they are easier to handle than the lower-boiling solvents which have to be used under pressure, such as carbon tetrachloride, chloroform or chlorethane.

If, however, the chlorination is performed in the second preferred temperature range of 30° to 90° C., a solvent is used in the reaction to dissolve the o-toluic acid. For this purpose, solvents having low boiling points are to be preferred, such as carbon tetrachloride, chloroform, methylene chloride, and chlorinated ethanes, which upon heating followed by cyclization can easily be removed again by distillation.

The chlorine is introduced as a gas through an immersed tube, through the bottom valve, or by absorption on the agitated surface. Bromine chloride can be used instead of chlorine, but only in rare cases is this desirable.

Long-wave ultraviolet light (e.g., >275 mm) is preferred as the initiator for this side-chain chlorination. The lamps can be submersible lamps or they can be mounted externally on a glass apparatus or an apparatus provided with glass windows, so as to radiate into the reaction chamber.

Also usable are chemical initiators such as peroxides or azo compounds, examples being dicumylperoxide, di-t-butyl peroxide, azoisobutyric acid nitrile or amidine, and others, such as are known for use in side-chain chlorination.

In accordance with the method, the degree of chlorination produced by the amount of chlorine added can amount to 0.1 to 2.5 moles of $Cl_2$ per mole of o-toluic acid.

A narrow low range and the high range of degrees of chlorination are preferred, because within them the working up and isolation can be accomplished more easily and more profitably by a single procedure, than it is in the medium range of degrees of chlorination, even though in that range large amounts of phthalide are formed directly.

Therefore, within the scope of the present invention, three methods of working up are greatly preferred.

In the first method of working up, the chlorination is performed at temperatures of 110° to 260° C. only to such an extent that 3-chlorophthalide occurs only in low concentrations of less than 5%, but a great amount of unchlorinated o-toluic acid is still present. The molar ratio of $Cl_2$ to o-toluic acid amounts in this procedure to 0.1 to 0.5:1, preferably 0.2 to 0.45:1, or, by weight, 0.05 to 0.26:1, preferably 0.10 to 0.23:1.

Since in these chlorination mixtures dihydrobiphthalyl occurs often in concentrations of about 7%, along with diphthalidyl ethers or other low-volatility compounds in some cases, it is desirable, for the purpose of obtaining a pure phthalide, to separate the raw mixture by the quick method of vacuum distillation. This method can also be used in the procedures to be described below.

All of the dihydrobiphthalyl remains in the sump of the still, and by additional chlorination it can be transformed almost entirely to 3-chlorophthalide.

This chlorination mixture can be worked up with aqueous, slightly alkaline solutions ranging from approximately pH 7.0 to 12, preferably 7.5 to 11, for example with 1 to 20 wt-% alkali bicarbonate or hydroxide solution, such as with NaOH solution for pH control, until all of the p-toluic acid has been dissolved mostly as alkali salt, and the small amounts of 3-chlorophthalide impurities have been saponified to phthalaldehydic acid. With thorough stirring at room temperature, this separation takes from 1 to 3 hours. Temperatures from 10° C. to 50° C. are utilizable.

The undissolved phthalide is filtered out, washed to neutral reaction, and dried. It immediately has a good purity of 98 to 99%. The yields range between 25 and 30%, with respect to the o-toluic acid put in, and therefore they are approximately 95% with respect to the phthalide in the chlorination mixture.

The alkaline filtrate is acidified, whereupon the o-toluic acid and any phthalide that has been dissolved precipitate. After filtration and drying, this o-toluic acid (60 to 70% of the input) can be reused for the chlorination.

The content of 3-chlorophthalide (3-CP) in this low-chlorinated mixture is so low that the phthaladehydic acid (PAA) formed from it by hydrolysis, which is approximately 2% soluble in water, remains in solution and does not impair the purity of the phthalide. If desired, the phthalaldehydic acid can be recovered and utilized.

Chlorination mixtures of a medium degree of chlorination of about 0.5 to 1.1 moles of $Cl_2$ per mole of o-toluic acid can be prepared and worked up, but they are feasible only if phthalide containing 3-CP or PAA is usable or residues of the starting material are acceptable. Here, again, refinement is possible, by a combination of the procedures mentioned above, but it is definitely more complicated.

In the second method of processing, o-toluic acid is chlorinated at temperatures of 110° to 260° C. until the sum of the phthalide and 3-chlorophthalide concentrations has reached the maximum of about 80 to 90%. This is the case when the molar ratio of $Cl_2$ to toluic acid is from 1.0 to 2.5:1, preferably 1.6 to 2.0:1, corresponding to weight ratios of $Cl_2$ to o-toluic acid of 0.52 to 1.30:1, preferably 0.83 to 1.04:1.

This mixture contains 10 to 40% of phthalide and 80 to 50% of 3-chlorophthalide, no o-toluic acid, and about 5% phthalic acid anhydride.

We have found that, in spite of the presence of phthalide, the working up can be accomplished by catalytic hydrogenation of the 3-CP with hydrogenation catalysts, especially noble metal catalysts, in the presence or absence of solvents, in accordance with German Offenlegungsschrift 26 14 294, in the absence or, in some cases, in the presence of HCl acceptors. (corresponding to Ser. No. 783,575 filed on Apr. 1, 1977.)

Preferably it is dissolved in xylene and, after the addition of palladium on $Al_2O_3$, it is catalytically hydrogenated until no more HCl appears in the exhaust gas. The chlorination mixture can first be distilled, resulting in a more rapid hydrogenation with equally high yields.

After the hydrogenation, the phthalide can be recovered in a conventional manner, for example by distillation or by crystallization after partial removal of the solvent.

The yields, with respect to the o-toluic acid put in, are around 75%, it being possible to obtain an additional 10%, approximately, by working up the mother liquors.

Preferably the crystallization from xylene is performed in the low temperature range of, for example, 0° to 20° C.

Phthalic acid anhydride causes no difficulty in these concentrations, since part of it is reduced to phthalide and part of it is removed upon the separation of the phthalide by crystallization.

The purities of the phthalide in both of the recovery procedures described amount to 98 to 99%, and therefore they attain a high level for phthalide without further refinement.

The chlorination mixture prepared at low temperatures of 30° to 110°, preferably 30° to 90° C., is worked up by a third method. In this case the chlorination is performed until the molar ratio of $Cl_2$ to o-toluic acid is 1.0 to 2.5:1, preferably 1.6 to 2.5:1, corresponding to the weight ratio of 0.52 to 1.30:1, preferably 0.83 to 1.30:1.

For the cyclization of the o-chloro- and o-dichloromethylbenzoic acid, which are the principal products, to phthalide and 3-chlorophthalide with the formation of HCl, the temperature is increased to 120° to 150° C. with continuing removal of the solvent by distillation, and this is continued until most of the HCl has been removed. This cyclized reaction mixture often has such a pure phthalide content that all that remains to be done is a fractional distillation, in which the last residue of the HCl is removed. The phthalide thus obtained still contains from 1 to 10% of 3-chlorophthalide, depending on the chlorination temperature and the amount of distillation performed, which need not cause any trouble, depending on the application—for example in the preparation of 3-bromophthalide—but which can be converted to phthalide by a normal catalytic hydrogenation as described in the second method of recovery, in which case excellent phthalide purities are obtained. The phthalide yields are around 75% of the theory with respect to o-toulic acid.

This method of procedure has all the advantages of a normal one-pot reaction.

The o-toluic acid put in does not have to have the highest purity, but can be contaminated to a great degree with phthalide, which forms as a by-product in the preparation of o-toluic acid, and which is more of a help than a hindrance to this procedure.

EXAMPLES

The following examples will serve to explain the invention.

Example 1

In a one-liter four-necked flask provided with stirrer, condenser, thermometer and a gas introduction tube, 408.4 grams of o-toluic acid (3 moles) are melted and heated at 180° C. An ultraviolet lamp (Philips, MLU 300 watts) is turned on and 520 grams of chlorine (7.35 moles) are introduced, with stirring, and after every 40 grams of chlorine is introduced a small sample is taken and analyzed by gas chromatography. In FIG. 1, the curves representing the most important components are plotted, namely o-toluic acid, phthalide and 3-chlorophthalide. The contents, expressed in flame ionization detector surface percentages (FID surface %), are substantially the same as the weight-percent, especially when they are high.

After the introduction of 360 to 400 g (5.07 to 5.64 moles) of chlorine, the sum of the phthalide plus 3-chlorophthalide attains a maximum of 90.0% plus 4 to 6% of phthalic acid anhydride and a number of other impurities (cf. Table 1).

Examples 2 to 6

In the same type of apparatus as is used in Example 1, 408.4 grams of o-toulic acid is chlorinated as described in Example 1 with 250 grams of chlorine gas, the samples are repeatedly taken for gas chromatography. The difference between the procedure of Example 1 and that of Example 2–6 is that the chlorination is performed at different temperatures, namely at 200° C. in Example 2, at 160° C. in Example 3, at 130° C. in Example 4, at 79°

C. using 1.1 liters of carbon tetrachloride in Example 5, and at 50° C. using 1.1 liters of carbon tetrachloride in Example 6.

Table 1

| Example No. | Temp. °C. | Amount of CL$_2$ in g | Gas chromatographic analysis of sample in FID surface % | | | | | | |
|---|---|---|---|---|---|---|---|---|---|
| | | | Ph | 3-CP | Ph + 3-CP | PAA | o-TA | o-CM | o-DCM |
| 1 a | 180 | 360 | 26.1 | 63.9 | 90.0 | 4.3 | 0 | 1.0 | 0.5 |
| b | | 400 | 13.9 | 76.3 | 90.2 | 6.8 | 0 | 0.1 | 0.3 |
| 2 * | 200 | 380 | 31.3 | 57.9 | 89.2 | 6.8 | 0 | 0 | 0.1 |
| 3 | 160 | 360 | 28.8 | 55.5 | 84.3 | 4.5 | 0 | 0.5 | 1.2 |
| 4 | 130 | 360 | 43.1 | 26.3 | 69.3 | 3.6 | 0 | 1.3 | 10.8 |
| 5 a | 79 | 105 | 31.4 | 0.4 | 31.8 | 0.1 | 29.2 | 36.4 | 1.9 |
| b | | 376 | 10.8 | 1.8 | 12.3 | 0.1 | 0.7 | 67.5 | 18.6 |
| 6 a | 50 | 187 | 26.6 | 0.2 | 26.8 | 0.5 | 11.1 | 57.3 | 4.5 |
| b | | 375 | 6.3 | 3.0 | 9.3 | 0.7 | 0.1 | 69.5 | 16.4 |

Ph = phthalide,
3-CP = 3-chlorophthalide,
PAA = phthalic acid anhydride,
o-TA = o-toluic acid,
o-CM = o-chloromethylbenzoic acid,
o-DCM = o-dichloromethylbenzoic acid.
* Yield = 462.5 g Table 1 lists the degree of chlorination at which the sum of Ph plus 3-CP reaches a maximum, which in Examples 1 to 4 occurs at 360 to 400 g of Cl$_2$ in 3 moles of o-toluic acid, and in Examples 5 and 6 is lower. The temperatures in Examples 5 and 6 (79° and 50° C., respectively) do not suffice for the cyclization of mono- and dichloromethylbenzoic acid, but, as shown in Examples 10 and 11, conversion to phthalide and to 3-CP, respectively, can be performed by increasing the temperature afterward.

Example 7

In a two-liter four-necked flask equipped with a stirrer, a condenser, a thermometer and a gas introduction tube, 1225 grams of o-toluic acid (9.0 moles) are heated at 180° C. Under radiation from an ultraviolet lamp, 1140 grams of chlorine gas (16.08 moles) are introduced.

Yield: 1380 g, with contents of 27.5% phthalide and 56.0% 3-CP (gas chromatography).

450 grams of this chlorination mixture are dissolved in 900 grams of xylene and hydrogenated with hydrogen gas for about 10 hours in a hydrogenation apparatus at 85° C. in the presence of palladium on Al$_2$O$_3$ as catalyst, until no more hydrogen chloride is present in the exhaust gas. The catalyst is filtered out and washed twice with 50 grams of xylene, and the filtrate is concentrated, by distilling out the xylene, to a solution containing approximately 60% of phthalide. The resultant solution is cooled to about 0° C., and the precipitate is filtered out and dried.

Yield: 289.2 g of phthalide (73.5% of the theory with respect to orthotoluic acid)
M.P.: 73–75% Purity; by titration with aqueous NaOH: 99%.

Example 8

In a two-liter four-necked flask equipped with stirrer, condenser, thermometer and gas introduction tube, 1225 g of o-toluic acid (9.0 moles) is reacted as in Example 6 with 1140 g of Cl$_2$ (16.08 moles) at 180° under radiation. 800 g of HCl (21.9 moles) is intercepted by absorption in water.

The chlorination mixture (1382 g, GC analysis: 34.2% phthalide, 56.7% 3-CO, 4.2% PAA) is distilled in a vacuum of 3 Torr at 108°–111° C. in the short method: 1294.6 g of distillate and 87.1 g of residue are obtained.

385 g of the distilled chlorination mixture is dissolved in 900 g of xylene and hydrogenated with hydrogen gas for about 5 hours in a hydrogenating apparatus at 85° in the presence of Pd on Al$_2$O$_3$ as catalyst. The catalyst was filtered out, washed twice with 50 g of xylene, and the filtrate was concentrated by distillation to a 60% solution of phthalide. The resultant solution is cooled to 0° C. and the cipitate is filtered out and dried. precipitate is filtered out and dried.

Yield: 273.5 g (75.0% with respect to o-toluic acid)
M.P.: 73°–75° C.
Purity by titration with aqueous NaOH: 99%
Purity per GC analysis: 98.4% phthalide; 1.6% PAA.

By concentration of the filtrate to dryness, treatment with 10% aqueous NaOH, extraction with chloriform and acidification of the aqueous solution, another 35 g, approximately, of phthalide is obtained (9.6% of the theory).

Example 9

In a two-liter four-necked flask equipped with stirrer, condenser, thermometer and gas introduction tube, 816 g of o-toluic acid (6.0 moles) is weighed in and heated at 180° C. Over a period of 3 hours, 180 g of chlorine gas (2.54 moles) is introduced. This mixture has the following GC composition:
68.4 FID surf.% o-toluic acid
23.1 FID surf.% phthalide
1.0 FID surf.% 3-chlorophthalide
7.5 FID surf.% dihydrobiphthalyl
185 grams of HCl is produced.

The chlorination mixture is distilled at a vacuum of 2 Torr and at 100°–115° C. for the quick removal of the dihydrobiphthalidyl, and 711 g distillate is obtained (90 g of residue). The distillate is stirred for 3 hours with a 10% soda solution at room temperature and then filtered, and the filter cake is again washed with soda solution and water, and dried. The filtrate is acidified with hydrochloric acid, the precipitate is filtered out and washed with water, and also dried.

| | Phthalide | o-Toluic acid |
|---|---|---|
| Yield | 220.8 g (27.5% of the theory) | 493.0 g (59.2% of the amount weighed in) |
| M.P. | 72°–74° C. | 98°–106° C. |
| GC Purity | 98.6% | 94.2% o-TA, 5.2% Ph |

Example 10

In a one-liter four-necked flask equipped with a stirrer, a condenser, a thermometer and a large-bore chlorine introduction tube, 272.3 g of o-toluic acid (2.0 moles) is dissolved in 730 g of CCl$_4$ at the temperature of ebullition (79° C.), and 275 g of Cl$_2$ (3.88 moles) is introduced. This mixture consists, according to gas chromatography, of 7.7% Ph, 0.5% 3-CP, 71.7% o-CM, and 19.7% o-DCM, and is heated at 120°–130° C. with gradual removal of CCl$_4$ by distillation, until no more formation of HCl occurs (yield: 300.0 g). It is then distilled at 110° C. and 3–4 Torr with the removal of a small amount of first runnings.

The yield is 211.3 g, which according to gas chromatography has the following composition: 88.8% PH, 10.0% 3-CP, plus 1% o-DCM.

The mixture is subjected to a catalytic hydrogenation, using the procedure as described in detail in Example 8.

Yield: 194.2 g (72.4% of the theory of phthalide, with respect to o-toluic acid)

M.P.: 74°–75° C.

Example 11

In a one-liter four-necked flask, provided with stirrer, thermometer and a large-bore chlorine introduction tube, 273.3 g of o-toluic acid (2.0 moles) is dissolved in 730 g of carbon tetrachloride at 50° C., and at this temperature, 355 g of chlorine gas (5.0 moles) is introduced. According to gas chromatography, the mixture is composed of: 6.0% Ph, 5.3% 3-CP, 1% o-TA, 75.0% o-CM, 11.5% o-DCM and a few unknown components.

Then the carbon tetrachloride is distilled off and the residue is heated at 120° to 130° C., until no more HCl was being formed (yield 275 g). It is distilled at 110° C. in a vacuum of 3–4 Torr, with the removal of a small amount of first runnings.

Yield: 201.8 g (75.22% of the theory of phthalide with respect to the orthotoluic acid)

According to gas chromatography, the distillate consists of 96.6% Ph, 2.2% 3-CP, and the balance of o-TA and o-DCM which can be hydrogenated to phthalide for the removal of the remainder of the 3-CP, without appreciable losses of yield.

What is claimed is:

1. The method for the preparation of phthalide which comprises chlorinating, in the melt or in an inert solvent, o-toluic acid with chlorine gas at a temperature of 110° to 260° C. with molar ratios of chlorine to o-toluic acid of (0.1 to 0.5):1, adjusting the pH of the reaction product to approximately 7.0 to 12 and filtering out the undissolved phthalide.

* * * * *

UNITED STATES PATENT AND TRADEMARK OFFICE
CERTIFICATE OF CORRECTION

PATENT NO. : 4,216,153
DATED : August 5, 1980
INVENTOR(S) : Klaus D. Steffen et al It is certified that error appears in the above-identified patent and that said Letters Patent are hereby corrected as shown below:

Column 1, line 8, "tempreatures" should be "temperatures".

Column 2, line 14, "yeild" should be "yield".

Column 3, line 52, "by", first occurence, should be "be".

Column 6, line 63, "250" should be "520".

Signed and Sealed this

Second Day of December 1980

[SEAL]

Attest:

SIDNEY A. DIAMOND

Attesting Officer

Commissioner of Patents and Trademarks